United States Patent [19]

Atcher et al.

[11] Patent Number: 5,030,441
[45] Date of Patent: Jul. 9, 1991

[54] METHOD OF MAKING COLLOID LABELED WITH RADIONUCLIDE

[75] Inventors: Robert W. Atcher, Chicago; John J. Hines, Glen Ellyn, both of Ill.

[73] Assignee: The United State of America as represented by the United States Department of Energy, Washington, D.C.

[21] Appl. No.: 580,450

[22] Filed: Sep. 11, 1990

Related U.S. Application Data

[62] Division of Ser. No. 358,732, May 30, 1989, Pat. No. 4,970,062.

[51] Int. Cl.⁵ .................... A61K 43/00; C09K 11/04
[52] U.S. Cl. .................................... 424/1.1; 252/625
[58] Field of Search .................. 252/634, 625, 635; 424/1.1

[56] References Cited

U.S. PATENT DOCUMENTS

Re. 29,066 12/1976 Evans .................................. 424/1.1
4,752,464 6/1988 Lieberman et al. .................. 424/1.1

OTHER PUBLICATIONS

Rotmensch et al., "The Developement of α-Emitting Radionuclide Lead-212", Am. J. Obstet. Gynecol, vol. 160, No. 4, Apr. 1989, pp. 789-797.

Primary Examiner—John S. Maples
Attorney, Agent, or Firm—James W. Weinberger; Thomas G. Anderson; William R. Moser

[57] ABSTRACT

A ferric hydroxide colloid having an alpha-emitting radionuclide essentially on the outer surfaces and a method of forming same. The method includes oxidizing a ferrous hydroxide to ferric hydroxide in the presence of a preselected radionuclide to form a colloid having the radionuclide on the outer surface thereof, and thereafter washing the colloid, and suspending the washed colloid in a suitable solution. The labelled colloid is useful in cancer therapy and for the treatment of inflamed joints.

27 Claims, No Drawings

METHOD OF MAKING COLLOID LABELED WITH RADIONUCLIDE

CONTRACTUAL ORIGIN OF THE INVENTION

The U.S. Government has rights in this invention pursuant to Contract No. W-31-109-ENG-38 between the U.S. Department of Energy and Argonne National Laboratory.

This is a division of application Ser. No. 358,732 filed May 30, 1989, now U.S. Pat. No. 4,970,062.

BACKGROUND OF THE INVENTION

This invention relates to the use of colloids labeled with alpha emitting radionuclide for a therapeutic use. Therapeutic uses contemplated includes treatment of rheumatoid arthritis, other inflammation of the joints, and cancer. Particularly, alpha emitting radionuclides are advantageously used for cancer therapy because they deliver high LET*, are lethal in absence of oxygen, and only penetrate a few cell diameters. Conventional cancer therapy employs surgery, radiation and chemotherapy. Each of these methods suffers a serious drawback in that it is not highly selective between healthy and cancerous cells. In order to be effective, these previous therapies kill or remove large amounts of healthy tissue. Furthermore, chemotherapy adversely affects the immune system so that death or serious illness often arises from fungal, bacteria or viral infections.

*linear energy transfer

The present therapy for rheumatoid arthritis includes aspirin, nonsteroidal anti-inflammatory agents, remission-inducing agents and intraarticular administration of corticosteroids. In some cases where medical therapy has been unsuccessful, surgical synovectomy has provided symptomatic relief for periods of from two to five years. Disadvantages of this later procedure, aside from the fact that the benefits are only temporary, are the risks of surgery and anesthesia, as well as the expense of prolonged hospitalization and intensive rehabilitation thereafter. Radiation synovectomy has been used extensively in Europe as an alternative to surgical synovectomy. Heretofore, it has been suggested that beta emitters be used for radiation synovectomy, but one of the problems is that the delivery systems for the radionuclide tend to leak out of the joint and thereafter deliver radiation to various parts of the body.

Alpha emitters are particularly advantageous, as heretofore stated because of the short range of the effect thereof which is advantageous not only in the treatment of work with radionuclides injected in the joints has encountered the problem of leaking of the radioactive material throughout the lymph system. Particularly, the inventive delivery system is advantageous because of the large colloid particles, which with the heavy alpha particles and short half life, represent an improvement in the art.

A problem inherent in the use of alpha emitters is the delivery system. Previous attempts to attach alpha emitters to colloids have resulted in alpha emitters which are uniformly distributed through the colloid material. Because of the relatively short distances in which alpha emitters are effective, distribution of alpha emitting radionuclides throughout a colloid results in a very low dose of radioactivity being delivered to the affected area.

We have found that by plating the radioactive nuclide onto the outer surfaces of the colloid vastly improved results have been obtained.

SUMMARY OF THE INVENTION

Accordingly, it is a principal objection of the invention to provide a colloid for the delivery of radionuclide material to preselected areas of the body.

It is another object of the invention to provide a ferric hydroxide colloid having a radionuclide essentially on the outer surfaces thereof.

It is still another object of the present invention to provide a method of forming a colloid with a radionuclide essentially on the outer surfaces thereof, the method comprising oxidizing a ferrous hydroxide to ferric hydroxide in the presence of a preselected radionuclide to form a colloid having the radionuclide on the surface thereof, washing the colloid, and suspending the washed colloid in a suitable solution.

It is a still further object of the present invention to provide a method of forming a colloid with a radionuclide of 212Pb for treatment of disease in a host, the method comprising, preparing a ferrous salt in an acid medium, adding sufficient hydroxide to the ferrous salt to convert the ferrous salt to ferrous hydroxide, oxidizing the ferrous hydroxide to ferric hydroxide in the presence of 212Pb to form a colloid having 212Pb essentially on the outer surfaces thereof, separating the colloid from the liquid and washing the colloid with pharmacologically compatible material, suspending the colloid in a solution suitable for injection into a host, and administering the colloid with the 212Pb to the disease situs.

A final object of the invention is to provide a method of treating inflammatory diseases of the joints comprising administering a ferric hydroxide colloid having an alpha emitting radionuclide essentially on the outer surfaces thereof to the diseased joint.

DETAILED DESCRIPTION OF THE INVENTION

As hereinbefore stated, the use of alpha emitters provides substantial advantages in the treatment of cancer. It is also possible to treat inflamed joints particularly rheumatoid arthritis with radioisotopes. For the reasons that alpha emitters are useful in the treatment of cancer, they are also useful in the treatment of arthritic joints. Radiation synovectomy has substantial advantages over the treatment by surgery, not the least which is that it can be repeated if the condition reoccurs. Other therapies often result in the eventual replacement of the joint. As before stated, radiation synovectomy suffers from leakage of the radioactive material from the joint. The use of alpha emitters which have a very short range of effectiveness is somewhat helpful in alleviating this condition, particularly when combined with the carrier hereinafter described.

Colloids labeled with radionuclide have been used in the past for the treatment of cancer and also for the treatment of rheumatoid arthritis. Because the alpha emitters are effective over a relatively short cellular range, labelling thereof with colloids has not been popular. This is particularly true where the radionuclide normally would be distributed evenly throughout the colloid because the distance that the alpha particles travel from the center of the colloid to the outside of the colloid is such that very little effective radiation remains to be delivered to the affected situs.

The use of colloids labeled with alpha emitting radionuclides are advantageously employed both for treating cancer cells and also for inflamed joints provided that there is some mechanism for plating the radionuclide essentially on the outer surface of the colloid and only on the outer surface. It has now been discovered that ferric hydroxide can be manipulated in such a way as to plate the radionuclide essentially on the outer surfaces of the colloid. Radionuclides which are useful in the present invention include 211Bi, 212Bi, 213Bi, 214Bi, 212Pb, 228Th, 224Ra, 211At, 254Esm, 238Np, 234Np, 242Am and various mixtures thereof. Many of these materials are produced in reactors or cyclotrons, but it is well within the skill of the art to manufacture and isolate the above listed alpha emitters. For instance, the preparation of various bismuth isotopes as well as the lead-212 is disclosed in the Atcher et al. U.S. Pat. No. 4,663,129, issued May 5, 1987, the disclosure of which is incorporated herein by reference. Methods of producing and separating astatine-211 as well as certain bismuth radioisotopes has been reported in the literature, see for instance *Appl. Radiat. Isot. Vol.* 39. No. 4, pp. 283-286, 1988, reporting a paper on radiation oncology. See also, *Official Journal of the American Rheumatism Association,* Arthritis and Rheumatism, Vol. 29, No. 2, February, 1986 in which the use of beta emitters for treatment of arthritic joints has been reported.

The colloid of the present invention must be prepared in such a manner that rather than having the radioactive isotope uniformly distributed throughout the colloid as is the usual circumstance, the radionuclide is essentially only on the outer surfaces thereof. In order to make this particular colloid, a ferrous salt such as a sulfate is treated with a hydroxide such as ammonium hydroxide to provide ferrous hydroxide. After the addition of radioactive 212Pb in the form of lead iodide, the ferrous hydroxide lead iodide mixture is mixed in air to oxidize the ferrous hydroxide to a ferric hydroxide colloid in which the lead isotope is attracted to and plates onto the outside surface of the colloid particles. The ferrous hydroxide may be formed either by starting with ferrous chloride or ferrous sulfate in an acid solution, such as a dilute hydrochloric acid. A suitable hydroxide such as ammonium hydroxide in reagent grade is used to convert the ferrous salt to the ferrous hydroxide. A vortex mixer is used to convert the ferrous hydroxide which does not attract the lead iodide in solution to ferric hydroxide which does attract the lead iodide in solution, the ferrous ion also converting the lead iodide to lead metal.

In a specific example, ferrous chloride at a concentration of 5mg/ml in dilute hydrochloric acid is mixed with a 2 molar solution of hydriodic acid containing lead212. Reagent grade ammonium hydroxide, 14.5 molar, is added to the mixture to form a bluish green ferrous hydroxide precipitate in a solution with the pH greater than 7. At this time the lead iodide remains in solution and is not attracted to the ferrous hydroxide particles. An air vortex mixer is used to agitate the ferrous hydroxide and lead iodide solution for approximately 30 seconds whereupon the bluish-green mixture disappears to be replaced by a dark yellow-brown mixture of ferric hydroxide which attracts the 212Pb to the surface principally as a metallic lead although a portion of the lead is present as lead hydroxide. This method of forming a colloid results in a ferric hydroxide colloid having radioactive 212Pb on the outer surface of the colloid either as lead metal or lead hydroxide and since the lead daughter, 212Bi, is an alpha emitter, provides a colloid with the most effective positioning of the radioisotope.

To study in-vivo the therapeutic effect of the intraperitoneal instillation of the radiocolloid, 212Pb ferrous hydroxide, the Ehrlich ascites carcinoma model was used. This carcinoma spontaneously arose in the ovary of the mouse. The carcinoma has been maintained by intraperitoneal inoculation and passage in Swiss-Webster mice. The virulence of the tumor was evaluated by inoculating groups of 10 mice ip with $10^0$ to $10^7$ cells. Survival was then measured from the day of inoculation. The therapeutic effect of ip administration of 212Pb ferrous hydroxide was evaluated by treating groups of 10 animals inoculated with $10^6$ cells with single graded doses of 0, 5, 15, and 50 uci's and measuring survival. The effect of delaying therapy was determined by observing survival in groups of 10 animals with $10^6$ cells treated with 50 uci's of the radiocolloid 48 and 72 hours later.

The cytotoxicity of 212Pb was compared to x-rays. Ehrlich carcinoma cells were grown in-vitro in 5cc of serum culture containing 72.5% Dulbecco's modification of Eagle's media, 22.5% Ham's nutrient mixture F-12, 5% fetal bovine serum, 20 mg/ml epidermal growth factor, 5 ug/ml transferrin, $2 \times 10^{-11}$M 3,3',5 triiodo-1-thyronine, $10^{-10}$M cholera toxin, $1.8 \times 10^{-4}$M adenine, 0.4 ug/ml hydrocortisone, 50 units/ml mycostatin, 100 u/ml penicillin, and 100 ug/ml streptomycin.

Survival experiments were done on exponentially growing cells. Cells were removed from flasks using trypsin suspended in serum containing media and seeded into 10 cm dishes at low density. Between 500 and 40,000 cells were plated and allowed to enter exponential growth.

To determine cellular survival after 212Pb irradiation, the radionuclide complexed to DPTA was diluted in complete culture medium. The activity of an aliquot was determined by counting the gamma rays in a spectrometer which was calibrated with a 228Th source. Cells were incubated at 37° C in media containing various radioactive concentrations of 212Pb DPTA. After the appropriate dose accumulated, the cells were washed and fed fresh media. Control incubations were done in an identical fashion except the 212Pb was replaced by 212Pb which had decayed to determine chemical toxicity.

For x-ray survival experiments cells were irradiated 18 hours after plating with a 250 kV Maxitron operating at 26 mA° at 0.8 Gy/min. Cultures were incubated for 18 to 24 days and then fixed and stained with crystal violet. Colonies greater than 50 were scored as survivors. Data points were analyzed by least square regression. The intrinsic radiosensitivity (Do) was defined as the inverse of the slope of the exponential portion of the survival curve. The cell s ability to accumulate sublethal damage was measured by the extrapolation number, n, which is the back extrapolation of the slope of the ordinate.

The Ehrlich carcinoma cells were extremely virulent. The intraperitoneal injection of graded doses from $10^0$ (1 cell) to $10^7$ cells caused ascites leading to the death of the animal within 57 to 58 days, respectively (Table 1) A tumor inoculum as small as 1 cell caused death in 80% of the animals. Treating animals 24 hours later inoculated with $10^6$ tumor cells with graded doses of 212Pb ferrous hydroxide prolonged survival. In the untreated inoculated animals the mean survival was 16 days. The mean survival after the injection of cold colloid along, 5, 15, or 50 uci's of the radiocolloid was 15, 49, 63, and 81 days, respectively (Table 2). The percentage of animals cured was related to the dose of the radionuclide administered. The cure rate was 0, 10, 23 and 40%, respectively for the doses administered. Delaying therapy to allow the tumor to progress decreasing survival. The mean survival in animals inoculated with $10^6$ cells decreased to 45 and 34 days by delaying treatment 48 or 72 hours, respectively.

In-vitro the Ehrlich cells were more radiosensitive to alpha particles than x-rays (Table 3). The survival curve had a steeper slope after 212Pb therapy. The radiosensitivity (Do) was 220 cGy after x-ray and 65 cGy after 212Pb irradiation. Cells which were able to accumulate sublethal damage after x-rays were unable to do so after 212Pb irradiation. There was a shoulder (n=1.7)- an indication of the ability of the cells to accumulate sublethal damage- present on the x-ray survival curve. With 212Pb treatment there was no shoulder (n=1) on the survival curve.

The intraperitoneal administration of 212Pb prolonged the median survival and produced cures in the Ehrlich ascites tumor model. This tumor was extremely virulent with the injection of one cell capable of producing tumor and death in the animals. The survival was dose related with higher doses of 15 and 50 uci's increasing survival threefold. The total eradication of tumor was seen in 24% of the animals injected with these doses. The most compelling reason for the increased effectiveness of these particles if the direct ionization over a very short path length without the dependence upon cellular oxygenation for cytotoxicity.

The use of these emitters may be most effective against microscopic disease. Tumor burden present appears to be an important factor when considering the use of these emitters. By delaying the intraperitoneal instillation of 212Pb up to 72 hours and allowing the tumor burden to increase both the survival and cure rates decreased.

Clinically alpha emitting radionuclides have the potential to be more efficacious than other beta-emitting radionuclides previously used such as gold-198 and phosphorus-32. The cellular radiosensitivity was markedly increased in comparison to conventional gamma (x-ray) irradiation. Survival was better with cells having no ability to accumulate sublethal danger after x-ray therapy. In comparison to beta-emitters, it is estimated that alpha irradiation has one-hundredth the range and may have up to ten times the energy deposition per unit path length making it more efficient in killing a tumor cell while perhaps sparing normal cells. As seen in the decay chain of 212Pb both beta and alpha particles are produced; however, considering that the total average energy per disintegration of 212Pb, the beta energy contribution to the dose is negligible.

TABLE 1.

Survival of animals inoculated with graded doses of Ehrlich ascites tumor cells.

| Number of cells injected | Days surviving | | | % Dead |
|---|---|---|---|---|
| | Minimum | Maximum | Mean | |
| $10^7$ | 8 | 18 | 14 | 100 |
| $10^6$ | 12 | 20 | 16 | 100 |
| $10^5$ | 17 | 29 | 18 | 100 |
| $10^4$ | 17 | 34 | 22 | 100 |
| $10^3$ | 19 | 28 | 23 | 100 |
| $10^2$ | 19 | 30 | 26 | 80 |
| $10^1$ | 28 | 38 | 33 | 80 |
| $10^0$ | 28 | 57 | 41 | 80 |

TABLE 2.

Survival and cure of animals inoculated with Ehrlich ascites tumor cells treated 24 hours later with lead-212 ferrous hydroxide.

| Tumor Inoculum | Treatment | Survival (Days) | | | % Cure |
|---|---|---|---|---|---|
| | | Min. | Max. | Mean | |
| $10^6$ | none | 12 | 20 | 16 | 0 |
| $10^6$ | cold colloid | 12 | 22 | 15 | 0 |
| $10^6$ | 5 uci 212Pb | 21 | 150 | 49 | 6 |
| $10^6$ | 15 uci 212Pb | 26 | 150 | 63 | 13 |
| $10^6$ | 50 uci 212Pb | 22 | 150 | 81 | 24 |

TABLE 3.

Summary of the radiosensitivities of Ehrlich carcinoma tumor cells to x-rays and lead-212.

| | Do | n |
|---|---|---|
| x-rays | 220 | 1.7 |
| 212Pb | 65 | 1 |

Do = radiosensitivity
n = ability to accumulate sublethal damage
RBE = relative biological effectiveness The use of these nuclides have the potential to add another treatment modality for microscopic carcinoma confined to the abdominal cavity. However, the concept is applicable to treatment of other types of carcinoma located in otherwise difficult areas. For instance, tumors of the liver are difficult to treat, but the colloid can be delivered through arterial blood flow to the liver, or for that matter, to any organ.

Delivery of the labelled colloid to inflamed joints, such as knees, fingers, toes and wrists promises an alternative therapy.

While there has been disclosed what is considered to be the preferred embodiment of the present invention, it is understood that various changes in the details may be made without departing from the spirit, or sacrificing any of the advantages of the present invention.

The embodiments of the invention in which an exclusive property or privilege is claimed are defined as follows:

1. A method of forming a colloid with a radionuclide essentially only on the outer surfaces thereof, said method comprising oxidizing a ferrous hydroxide to ferric hydroxide in the presence of a preselected radionuclide to form a colloid having the radionuclide on the surface thereof, washing the colloid, and suspending the washed colloid in a pharmacologically acceptable solution.

2. The method of claim 1, wherein the ferrous hydroxide is oxidized to ferric hydroxide by contact with air.

3. The method of claim 1, wherein the radionuclide is selected from the group consisting of 211Bi, 212Bi, 213Bi, 214Bi, 212Pb, 228Th, 224Ra, 211At, 254Esm, 238Np, 234Np, 242Am and mixtures thereof.

4. The method of claim 2, wherein the radionuclide is 212Pb.

5. The method of claim 3, wherein the solution is pharmacologically acceptable to a warm blooded animal.

6. The method of claim 5, and further comprising administering the solution to a human by injection.

7. A method of forming a colloid with a radionuclide of 212Pb for treatment of disease in a host, said method comprising, preparing a ferrous salt in an acid medium, adding sufficient hydroxide to the ferrous salt to convert the ferrous salt to ferrous hydroxide, oxidizing the ferrous hydroxide to ferric hydroxide in the presence of Pb212 to form a colloid having 212Pb essentially only on the outer surfaces thereof, separating the colloid from the liquid and washing the colloid with pharmacologically compatible material, suspending the colloid in a solution suitable for injection into a host, and administering the colloid with the 212Pb to the disease situs.

8. The method of claim 7, wherein the ferrous salt is ferrous chloride, and the acid medium contains hydrochloric acid.

9. The method of claim 7, wherein the 212Pb is present as lead iodide and the hydroxide is ammonium hydroxide.

10. The method of claim 9, wherein the lead iodide is present when the ferrous chloride is converted to ferrous hydroxide.

11. The method of claim 9, wherein lead iodide is added after the ferrous hydroxide is formed.

12. A method of forming a colloid with a radionuclide essentially only on the outer surface thereof and administering said colloid to a person in need thereof, said method comprising oxidizing a ferrous hydroxide to ferric hydroxide in the presence of a preselected radionuclide to form a colloid having the radionuclide only essentially on the surface thereof, washing the colloid, suspending the washed colloid in a pharmacologically acceptable solution, and administering the solution to the person by injection.

13. The method of claim 12, wherein the ferrous hydroxide is oxidized to ferric hydroxide by contact with air.

14. The method of claim 12, wherein the radionuclide is selected from the group consisting of 211Bi, 212Bi, 213Bi, 214Bi, 212Pb, 228Th, 224Ra, 211At, 254Esm, 238Np, 234Np, 242Am and mixtures thereof.

15. The method of claim 13, wherein the radionuclide is 212Pb.

16. A method of forming a colloid with a radionuclide of 212Pb for treatment of disease in a host, said method comprising, preparing a ferrous salt in an acid medium, adding sufficient hydroxide to the ferrous salt to convert the ferrous salt to ferrous hydroxide, oxidizing the ferrous hydroxide to ferric hydroxide in the presence of Pb212 to form a colloid having 212Pb only essentially on the outer surfaces thereof, separating the colloid from the liquid and washing the colloid with pharmacologically compatible material, suspending the colloid in a solution suitable for injection into a host, and administering the colloid with the 212Pb by injection tot he disease situs.

17. The method of claim 16, wherein the ferrous salt is ferrous chloride, and the acid medium contains hydrochloric acid.

18. The method of claim 16, wherein the 212Pb is present as lead iodide and the hydroxide is ammonium hydroxide.

19. The method of claim 16, wherein the lead iodide is present when the ferrous chloride is converted to ferrous hydroxide.

20. The method of claim 16, wherein lead iodide is added after the ferrous hydroxide is formed.

21. The method of claim 16, wherein the host has cancer cells and the colloid is administered to the situs of the cancer cells in a therapeutically effective amount for a time sufficient to kill the cancer cells present.

22. The method of claim 21, wherein the colloid is administered in divided doses.

23. The method of claim 21, wherein the cancer cells are located in the peritoneal cavity.

24. The method of claim 21, wherein the cancer calls are located in the spinal column.

25. The method of claim 21, wherein the cancer cells are located in the liver.

26. The method of claim 21, wherein the cancer cells are located in pleural effusions.

27. The method of claim 21, wherein the colloid is injected into an artery in fluid communication with an organ infected with cancer.

* * * * *